United States Patent [19]

Mark et al.

[11] Patent Number: 4,853,332

[45] Date of Patent: Aug. 1, 1989

[54] STRUCTURAL GENES, PLASMIDS AND TRANSFORMED CELLS FOR PRODUCING CYSTEINE DEPLETED MUTEINS OF BIOLOGICALLY ACTIVE PROTEINS

[75] Inventors: David F. Mark, Danville; Leo S. Lin, Fremont; Shi-Da Yu Lu, Oakland, all of Calif.

[73] Assignee: Cetus Corporation, Emeryville, Calif.

[21] Appl. No.: 684,483

[22] Filed: Dec. 21, 1984

Related U.S. Application Data

[60] Division of Ser. No. 564,224, Dec. 20, 1983, Pat. No. 4,518,584, which is a continuation-in-part of Ser. No. 486,162, Apr. 15, 1983, abandoned, which is a continuation-in-part of Ser. No. 435,154, Oct. 19, 1982, abandoned.

[30] Foreign Application Priority Data

Oct. 10, 1983 [IE] Ireland .................................. 2380/83

[51] Int. Cl.⁴ ........................ C12N 1/20; C12N 15/00; C07H 21/04
[52] U.S. Cl. ............................... 435/252.33; 435/320; 435/172.3; 435/68; 435/252.1; 536/27
[58] Field of Search ...................... 435/68, 172.3, 253, 435/317, 240.2, 240.4, 255, 252.33, 252.1; 536/27

[56] References Cited

U.S. PATENT DOCUMENTS

| | | | |
|---|---|---|---|
| 4,315,852 | 2/1982 | Leibowitz et al. | 435/811 |
| 4,390,623 | 6/1983 | Fabricius et al. | 424/85 |
| 4,401,756 | 8/1983 | Gillis | 435/68 |
| 4,448,879 | 5/1984 | Fabricius et al. | 435/68 |
| 4,450,103 | 5/1984 | Konrad et al. | 260/112 R |
| 4,462,940 | 7/1984 | Hanisch et al. | 435/68 |
| 4,464,295 | 8/1984 | Laduri et al. | 260/112 R |
| 4,464,355 | 8/1984 | Fabricius et al. | 424/101 |
| 4,476,049 | 10/1984 | Kung | 260/112 R |
| 4,490,289 | 12/1984 | Stern et al. | 260/112 |
| 4,511,502 | 4/1984 | Builder et al. | 260/112 R |
| 4,511,503 | 4/1985 | Olson et al. | 260/112 R |
| 4,512,922 | 4/1985 | Jones et al. | 260/112 R |
| 4,518,584 | 5/1985 | Mark et al. | 425/85 |
| 4,530,787 | 7/1985 | Shaked et al. | 260/112 R |
| 4,564,593 | 1/1986 | Tsukamoto et al. | 435/91 |
| 4,569,790 | 2/1986 | Koths et al. | 260/112 R |
| 4,572,798 | 2/1986 | Koths et al. | 260/112 R |
| 4,738,927 | 4/1988 | Taniguchi et al. | 435/243 |

FOREIGN PATENT DOCUMENTS

| | | |
|---|---|---|
| 0088195 | 9/1983 | European Pat. Off. . |
| 0091539 | 10/1983 | European Pat. Off. . |
| 0092163 | 10/1983 | European Pat. Off. . |
| 0094317 | 11/1983 | European Pat. Off. . |
| 0111344 | 6/1984 | European Pat. Off. . |
| 0118617 | 9/1984 | European Pat. Off. . |
| 0118977 | 9/1984 | European Pat. Off. . |
| 0119621 | 9/1984 | European Pat. Off. . |
| 0121352 | 10/1984 | European Pat. Off. . |
| 0128467 | 12/1984 | European Pat. Off. . |
| 0132359 | 1/1985 | European Pat. Off. . |
| 0142268 | 5/1985 | European Pat. Off. . |
| 0145390 | 6/1985 | European Pat. Off. . |
| 0147819 | 7/1985 | European Pat. Off. . |
| 0158198 | 10/1985 | European Pat. Off. . |
| 0158487 | 10/1985 | European Pat. Off. . |
| 0148098 | 11/1980 | Japan . |

OTHER PUBLICATIONS

Stern, A., et al., Proc. Natl. Acad. Sci., vol. 81, pp. 871–875, 1984.

Altman, A., et al., Proc. Natl. Acad. Sci., vol. 81, pp. 2176–2180, 1984.

(List continued on next page.)

*Primary Examiner*—Blondel Hazel
*Attorney, Agent, or Firm*—Philip L. McGarrigle; Albert P. Halluin; Thomas E. Ciotti

[57] ABSTRACT

Muteins of biologically active proteins such as IFN-$\beta$ and IL-2 in which cysteine residues that are not essential to biological activity have been deleted or replaced with other amino acids to eliminate sites for intermolecular crosslinking or incorrect intramolecular disulfide bridge formation. These muteins are made via bacterial expression of mutant genes that encode the muteins that have been synthesized from the genes for the parent proteins by oligonucleotide-directed mutagenesis.

17 Claims, 15 Drawing Sheets

OTHER PUBLICATIONS

Shrorski et al., Proc. Natl. Acad. Sci., vol. 81, pp. 7544–7548, 1984.
Welte, K., et al., *J. Exp. Med.,* (1982), 156:454–464.
*Lymphokine Res.,* (1982), I(2), FASEB Editorial.
Coughlin, R. T. et al., *Federation Proceedings,* (1983), 42(7):2022.
Devos et al., *Nucleic Acid Res.,* (1983), 11(13):4307.
Henderson et al., *J. Immunol.,* (1983), 131(2):810–815.
Milstone et al., *Biochem. Biophy. Res. Comm.,* (1983), 115(3):762–768.
Mochizuki et al., *J. Immuno. Meth.,* (1980), 39:185–201.
Henriksen et al., *Cell Immunol.,* (1982), 73:106–114.
Ihle et al., *J. Immunol.,* (1982), 129(6):2431.
Watson, et al., *J. Exp. Med.,* (1979), 150:849–861.
Derynck et al., *Nature,* (1980), 287:193–197.
Gillis et al., *J. Immunol.,* (1980), 124:1954–1962.
Riendeau et al., *J.B.C.,* (1983), 258(20):12114–12117.
Taniguchi et al., *Nature,* (1983), 302:305.
Robb, R. J., *Immunology Today,* (1984), 5(7):203.
Rosenburg, S. A., *Science,* (1984), 223:1412.
Stern, A. S., et al., *Proc. Natl. Acad. Sci.,* (USA), (1984), 81:871–875.
Wang, Alice, et al., *Science,* 224:1431–1433.
"Chromatographic Removal of Pyrogens," *Bio/Technology,* Dec. 1984, 1035–1038.
Lahm et al., *J. of Chromatography,* (1985), 326:357–361.
Rosenberg et al., *New England Journal of of Medicine,* (1985), 313:1485–1492.

|  | 5 | 10 | 15 | 20 |
|---|---|---|---|---|
| | MetSerTyrAsnLeu | LeuGlyPheLeuGln | ArgSerSerAsnPhe | GlnCysGlnLysLeu |
| | 25 | 30 | 35 | 40 |
| | LeuTrpGlnLeuAsn | GlyArgLeuGluTyr | CysLeuLysAspArg | MetAsnPheAspIle |
| | 45 | 50 | 55 | 60 |
| | ProGluGluIleLys | GlnLeuGlnGlnPhe | GlnLysGluAspAla | AlaLeuThrIleTyr |
| | 65 | 70 | 75 | 80 |
| | GluMetLeuGlnAsn | IlePheAlaIlePhe | ArgGlnAspSerSer | SerThrGlyTrpAsn |
| | 85 | 90 | 95 | 100 |
| | GluThrIleValGlu | AsnLeuLeuAlaAsn | ValTyrHisGlnIle | AsnHisLeuLysThr |
| | 105 | 110 | 115 | 120 |
| | ValLeuGluGluLys | LeuGluLysGluAsp | PheThrArgGlyLys | LeuMetSerSerLeu |
| | 125 | 130 | 135 | 140 |
| | HisLeuLysArgTyr | TyrGlyArgIleLeu | HisTyrLeuLysAla | LysGluTyrSerHis |
| | 145 | 150 | 155 | 160 |
| | CysAlaTrpThrIle | ValArgValGluIle | LeuAgAsnPheTyr | PheIleAsnArgLeu |
| | 165 | 170 | 175 | 180 |
| | ThrGlyTyrLeuArg | Asn--- | | |

FIG. 1

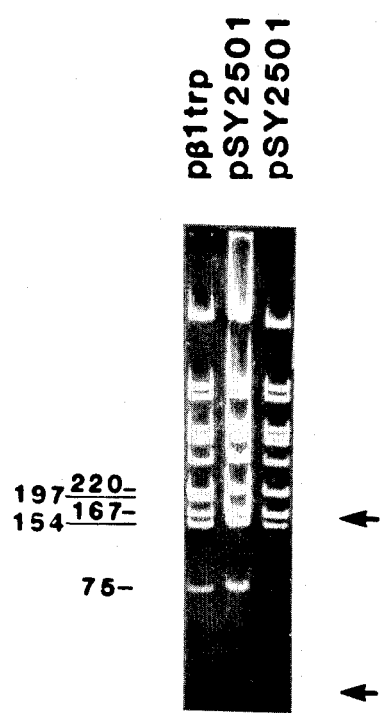
FIG. 8a
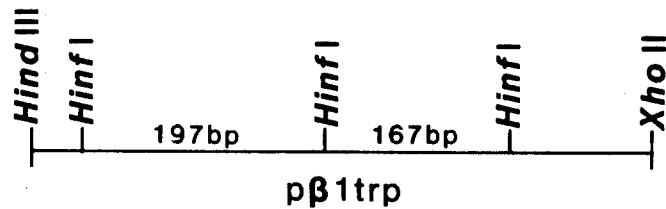
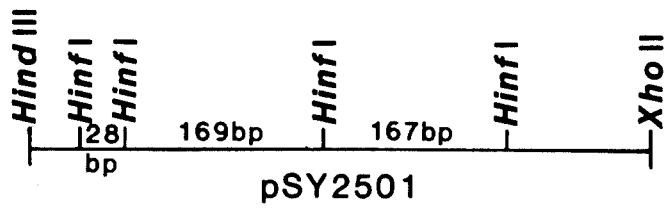
FIG. 8b

IFN-B CYS TO SER CHANGE AT AMINO ACID 17

```
1                                                              17
ATG AGC TAC AAC TTG CTT GGA TTC CTA CAA AGA AGC AGC AAT TTT CAG AGT CAG AAG CTC
met ser tyr asn leu leu gly phe leu gln arg ser ser asn phe gln ser gln lys leu 61
CTG TGG CAA TTG AAT GGG AGG CTT GAA TAT TGC CTC AAG GAC AGG ATG AAC TTT GAC ATC
leu trp gln leu asn gly arg leu glu tyr cys leu lys asp arg met asn phe asp ile 121
CCT GAG GAG ATT AAG CAG CTG CAG CAG TTC CAG AAG GAG GAC GCC GCA TTG ACC ATC TAT
pro glu glu ile lys gln leu gln gln phe gln lys glu asp ala ala leu thr ile tyr 181
GAG ATG CTC CAG AAC ATC TTT GCT ATT TTC AGA CAA GAT TCA TCT AGC ACT GGC TGG AAT
glu met leu gln asn ile phe ala ile phe arg gln asp ser ser ser thr gly trp asn 241
GAG ACT ATT GTT GAG AAC CTC CTG GCT AAT GTC TAT CAT CAG ATA AAC CAT CTG AAG ACA
glu thr ile val glu asn leu leu ala asn val tyr his gln ile asn his leu lys thr 301
GTC CTG GAA GAA AAA CTG GAG AAA GAA GAT TTC ACC AGG GGA AAA CTC ATG AGC AGT CTG
val leu glu glu lys leu glu lys glu asp phe thr arg gly lys leu met ser ser leu 361
CAC CTG AAA AGA TAT TAT GGG AGG ATT CTG CAT TAC CTG AAG GCC AAG GAG TAC AGT CAC
his leu lys arg tyr tyr gly arg ile leu his tyr leu lys ala lys glu tyr ser his 421
TGT GCC TGG ACC ATA GTC AGA GTG GAA ATC CTA AGG AAC TTT TAC TTC ATT AAC AGA CTT
cys ala trp thr ile val arg val glu ile leu arg asn phe tyr phe ile asn arg leu 481
ACA GGT TAC CTC CGA AAC TGA AGA TC
thr gly tyr leu arg asn ***
```

FIG. 10

```
              10         20         30         40         50         60
       ATGCCTACTT CAAGTTCTAC AAAGAAAACA CAGCTACAAC TGGAGCATTT ACTGCTGGAT
              70         80         90        100        110        120
       TTACAGATGA TTTTGAATGG AATTAATAAT TACAAGAATC CCAAACTCAC CAGGATGCTC
             130        140        150        160        170        180
       ACATTTAAGT TTTACATGCC CAAGAAGGCC ACAGAACTGA AACATCTTCA GTGTCTAGAA
             190        200        210        220        230        240
       GAAGAACTCA AACCTCTGGA GGAAGTGCTA AATTTAGCTC AAAGCAAAAA CTTTCACTTA
             250        260        270        280        290        300
       AGACCCAGGG ACTTAATCAG CAATATCAAC GTAATAGTTC TGGAACTAAA GGGATCTGAA
             310        320        330        340        350        360
       ACAACATTCA TGTGTGAATA TGCTGATGAG ACAGCAACCA TTGTAGAATT TCTGAACAGA
             370        380        390        400        410        420
       TGGATTACCT TTTCTCAGAG CATCATCTCA ACACTGACTT GA
```

FIG. 15a

```
                      5                 10                 15                 20
       MetProThrSerSer SerThrLysLysThr GlnLeuGlnLeuGlu HisLeuLeuLeuAsp
                     25                 30                 35                 40
       LeuGlnMetIleLeu AsnGlyIleAsnAsn TyrLysAsnProLys LeuThrArgMetLeu
                     45                 50                 55                 60
       ThrPheLysPheTyr MetProLysLysAla ThrGluLeuLysHis LeuGlnCysLeuGlu
                     65                 70                 75                 80
       GluGluLeuLysPro LeuGluGluValLeu AsnLeuAlaGlnSer LysAsnPheHisLeu
                     85                 90                 95                100
       ArgProArgAspLeu IleSerAsnIleAsn ValIleValLeuGlu LeuLysGlySerGlu
                    105                110                115                120
       ThrThrPheMetCys GluTyrAlaAspGlu ThrAlaThrIleVal GluPheLeuAsnArg
                    125                130                135                140
       TrpIleThrPheSer GlnSerIleIleSer ThrLeuThr---
```

FIG. 15b

STRUCTURAL GENES, PLASMIDS AND TRANSFORMED CELLS FOR PRODUCING CYSTEINE DEPLETED MUTEINS OF BIOLOGICALLY ACTIVE PROTEINS

CROSS-REFERENCE TO RELATED APPLICATION

This application is division of U.S. Ser. No. 564,224 filed Dec. 20, 1983, now U.S. Pat. No. 4,518,584, which in turn is a continuation-in-part of U.S. Ser. No. 486,162 filed Apr. 15, 1983, now abandoned, which is a continuation-in-part of U.S. Ser. No. 435,154 filed Oct. 19, 1982, now abandoned.

DESCRIPTION

1. Technical Field

This invention is in the general area of recombinant DNA technology. More specifically it relates to mutationally altered biologically active proteins that differ from their parent analogs by one or more substitutions/deletions of cysteine residues.

2. Background Art

Biologically active proteins that are microbially produced via recombinant DNA (rDNA) technology may contain cysteine residues that are nonessential to their activity but are free to form undesirable intermolecular or intramolecular links. One such protein is microbially produced human beta interferon (IFN-$\beta$). In the course of the preparation of IFN-$\beta$ by rDNA techniques, it has been observed that dimers and oligomers of microbially produced IFN-$\beta$ are formed in E. coli extracts containing high concentrations of IFN-$\beta$. This multimer formation renders purification and separation of IFN-$\beta$ very laborious and time-consuming and necessitates several additional steps in purification and isolation procedures such as reducing the protein during purification and reoxidizing it to restore it to its original conformation, thereby increasing the possibility of incorrect disulfide bond formation. Furthermore, microbially produced IFN-$\beta$ has also been found to exhibit consistently low specific activity due perhaps to the formation of multimers or of random intramolecular disulfide bridges. It would be desirable, therefore, to be able to alter microbially produced biologically active proteins such as IFN-$\beta$ in a manner that does not affect their activity adversely but reduces or eliminates their ability to form intermolecular crosslinks or intramolecular bonds that cause the protein to adopt an undesirable tertiary structure (eg, a conformation that reduces the activity of the protein).

The present invention is directed to producing by directed mutagenesis techniques mutationally altered biologically active proteins (such proteins are called "muteins", *Glossary of Genetics and Cytogenetics*, 4th ED, p 381, Springer-Verlag (1976)) that retain the activity of their parent analogs but lack the ability to form intermolecular links or undesirable intramolecular disulfide bonds. In this regard Shepard, H. M., et al, *Nature* (1981) 294: 563-565 describe a mutein of IFN-$\beta$ in which the cysteine at position 141 of its amino acid sequence (there are three cysteines in native human IFN-$\beta$ at positions 17, 31, and 141, *Gene* (1980) 10: 11-15 and *Nature* (1980) 285: 542-547) is replaced by tyrosine. This mutein was made by bacterial expression of a hybrid gene constructed from a partial IFN-$\beta$ cDNA clone having a G→A transition at nucleotide 485 of the IFN-$\beta$ gene. The mutein lacked the biological activity of native IFN-$\beta$ leading the authors to conclude that the replaced cysteine was essential to activity.

Directed mutagenesis techniques are well known and have been reviewed by Lather, R. F. and Lecoq, J. P. in *Genetic Engineering* Academic Press (1983) pp 31-50. Oligonucleotide-directed mutagenesis is specifically reviewed by Smith, M. and Gillam, S. in *Genetic Engineering: Principles and Methods*, PLenum Press (1981) 3: 1-32.

DISCLOSURE OF THE INVENTION

One aspect of the invention is a synthetic mutein of a biologically active protein which protein has at least one cysteine residue that is free to form a disulfide link and is nonessential to said biological activity, said mutein having at least one of said cysteine residues deleted or replaced by another amino acid.

Another aspect of the invention relates to synthetic structural genes having DNA sequences that have been specifically designed ("designer genes") to encode the above described synthetic muteins. Subaspects of this aspect are expression vectors that include such structural designer genes, host cells or organisms transformed with such vectors, and processes for making the synthetic mutein by culturing such transformants or their progeny and recovering the mutein from the culture. In the case of muteins that have therapeutic utility, therapeutic compositions that contain therapeutically effective amounts of the muteins and therapeutic methods are other aspects of the invention.

Another aspect of the invention is a method of preventing a protein having one or more cysteine residues that is free to form an undesirable disulfide link from forming such a link comprising mutationally altering the protein by deleting the cysteine residue(s) or replacing them other amino acids.

Still another aspect of the invention is a method for making the above described synthetic structural gene by oligonucleotide-directed mutagenesis comprising the following steps:

(a) hybridizing single-stranded DNA comprising a strand of a structural gene that encodes the parent protein with a mutant oligonucleotide primer that is complementary to a region of the strand that includes the codon for the cysteine to be deleted or replaced or the antisense triplet paired with the codon, as the case may be, except for a mismatch with that codon or antisense triplet, as the case may be, that defines a deletion of the codon or a triplet that encodes said other amino acid;

(b) extending the primer with DNA polymerase to form a mutational heteroduplex; and (c) replicating the mutational heteroduplex.

The mutant oligonucleotide primers used in this process are another aspect of the invention.

BRIEF DESCRIPTION OF THE DRAWINGS

FIG. 1 is a diagram of the amino acid sequence of IFN-$\beta$.

FIG. 8a shows the HinfI restriction pattern of clone pSY2501 and FIG. 8b shows the resulting two 169bp and 28bp fragments thereof.

FIG. 10 shows the coding DNA sequence for the mutein IFN-$\beta_{ser17}$ with the corresponding amino acid sequence therefor.

FIGS. 15a and 15b show, respectively, the nucleotide sequence of the coding strand of the clone pLW46 and the corresponding amino acid sequence of the IL-2 mutein designated IL-2$_{ser125}$.

MODES FOR CARRYING OUT THE INVENTION

Figure 2:
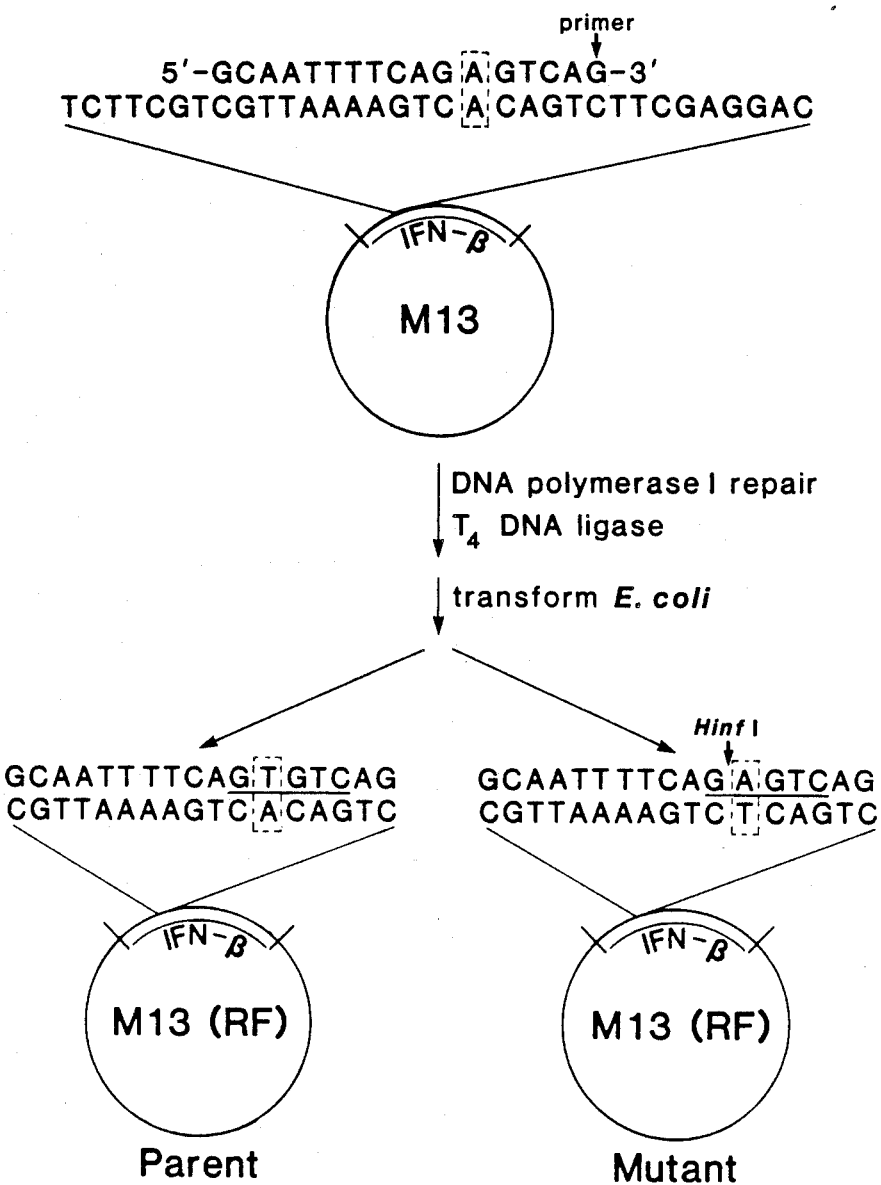
FIG. 2 is a schematic illustration showing the preparation of mutant IFN-$\beta$ gene by oligonucleotide-directed mutagenesis.

The present invention provides: muteins of biologically active proteins in which cysteine residues that are not essential to biological activity have been deliberately deleted or replaced with other amino acids to eliminate sites for intermolecular crosslinking or incorrect intramolecular disulfide bond formation; mutant genes coding for such muteins; and means for making such muteins.

Proteins that may be mutationally altered according to this invention may be identified from available information regarding the cysteine content of biologically active proteins and the roles played by the cysteine residues with respect to activity and tertiary structure. For proteins for which such information is not available in the literature this information may be determined by systematically altering each of the cysteine residues of the protein by the procedures described herein and testing the biological activity of the resulting muteins and their proclivity to form undesirable intermolecular or intramolecular disulfide bonds. Accordingly, while the invention is specifically described and exemplified below as regards muteins of IFN-$\beta$ and IL-2 it will be appreciated that the following teachings apply to any other biologically active protein that contains a functionally nonessential cysteine residue that makes the protein susceptible to undesirable disulfide bond formation. Examples of proteins other than IFN-$\beta$ and IL-2 that are candidates for mutational alteration according to the invention are lymphotoxin (tumor necrosis factor), colony stimulating factor-1, and IFN-$\alpha$1. Candidate proteins will usually have an odd number of cysteine residues.

In the case of IFN-$\beta$ it has been reported in the literature and that both the glycosylated and unglycosylated IFNs show qualitatively similar specific activities and that, therefore, the glycosyl moieties are not involved in and do not contribute to the biological activity of IFN-$\beta$. However, bacterially produced IFN-$\beta$ which is unglycosylated consistently exhibits quantitatively lower specific activity than native IFN-$\beta$ which is glycosylated. IFN-$\beta$ is known to have three cysteine residues at positions 17, 31 and 141. Cysteine 141 has been demonstrated by Shepard, et al, supra, to be essential for biological activity. In IFN-$\alpha$, which contains four cysteine residues, there are two intramolecular —S—S— bonds: one between cys 29 and cys 138 and another between cys 1 and cys 98. Based on the homology between IFN-$\beta$ and IFN-$\alpha$s cys 141 of IFN-$\beta$ could be involved in an intramolecular —S—S— bond with cys 31, leaving cys 17 free to form intermolecular crosslinks. By either deleting cys 17 or subsituting it by a different amino acid, onc can determine whether cys 17 is essential to biological activity, and its role in —SS— bond formation. If cys 17 is not essential for the biological activity of the protein, the resulting cys 17-deleted or cys 17-substituted protein might exhibit specific activity close to that of native IFN-$\beta$ and would possibly also facilitate isolation and purification of the protein.

By the use of the oligonucleotide-directed mutagenesis procedure with a synthetic oligonucleotide primer that is complementary to the region of the IFN-$\beta$ gene at the codon for cys 17 but which contains single or multiple base changes in that codon, a designer gene may be produced that results in cys 17 being replaced with any other amino acid of choice. When deletion is desired the oligonucleotide primer lacks the codon for cys 17. Conversion of cys 17 to neutral amino acids such as glycine, valine, alanine, leucine, isoleucine, tyrosine, phenylalanine, histidine, tryptophan, serine, threonine and methionine is the preferred approach. Serine and threonine are the most preferred replacements because of their chemical analogy to cysteine. When the cysteine is deleted, the mature mutein is one amino acid shorter than the native parent protein or the microbially produced IFN-$\beta$.

Human IL-2 is reported to have three cysteine residues located at positions 58, 105, and 125 of the protein. As in the case of IFN-$\beta$, IL-2 is in an aggregated oligomeric form when isolated from bacterial cells and has to be reduced with reducing agents in order to obtain a good yield from bacterial extracts. In addition, the purified reduced IL-2 protein is unstable and readily reoxidized upon storage to an oligomeric inactive form. The presence of three cysteines means that upon reoxidation, the protein may randomly form one of three possible intramolecular disulfide bridges, with only one of those being the correct bridge as found in the native molecule. Since the disulfide structure of the native IL-2 protein is not known, it is possible to use the present invention to create mutations at codons 58, 105 and 125 of the IL-2 gene and identify which cysteine residues are necessary for activity and therefore most likely to be involved in native disulfide bridge formation. In the same vein, the cysteine residue that is not necessary for activity can be modified so as to prevent the formation of incorrect intramolecular disulfide bridges and minimize the chance of intermolecular disulfide bridges by replacement of the free cysteine residue.

The size of the oligonucleotide primer is determined by the requirement for stable hybridization of the primer to the region of the gene in which the mutation is to be induced, and by the limitations of the currently available methods for synthesizing oligonucleotides. The factors to be considered in designing oligonucleotides for use in oligonucleotide-directed mutagenesis (eg, overall size, size of portions flanking the mutation site) are described by Smith, M. and Gillam S., supra. In general the overall length of the oligonucleotide will be such as to optimize stable, unique hybridization at the mutation site with the 5' and 3' extensions from the mutation site being of sufficient size to avoid editing of the mutation by the exonuclease activity of the DNA polymerase. Oligonucleotides used for mutagenesis in accordance with the present invention usually contain from about 12 to about 24 bases, preferably from about 14 to about 20 bases and still more preferably from about 15 to about 18 bases. They will usually contain at least about three bases 3' of the altered or missing codon.

The method for preparing the modified IFN-$\beta$ gene broadly involves inducing a site-specific mutagenesis in the IFN-$\beta$ gene at codon 17 (TGT) using a synthetic nucleotide primer which omits the codon or alters it so that it codes for another amino acid. When threonine replaces the cysteine and the primer is hybridized to the antisense strand of the IFN-$\beta$ gene, the preferred nucleotide primer is GCAATTTTCAGACTCAG (underlining denotes the altered codon). When it is desirable to delete cysteine, the preferred primer is AGCAATTTTCAGCAGAAGCTCCTG, which omits the TGT codon for cys. When cysteine is replaced by serine, a 17-nucleotide primer, GCAATTTTCAGAGTCAG, which includes an AGT codon for serine is the primer of choice. The T→A transition of the first base in the cys 17 codon results in changing cysteine to serine. It must be recognized that when deletions are introduced, the proper reading frame for the DNA sequence must be maintained for expression of the desired protein.

The primer is hybridized to single-stranded phage such as M13, fd, or $\emptyset$X174 into which a strand of the IFN-$\beta$ gene has been cloned. It will be appreciated that the phage may carry either the sense strand or antisense strand of the gene. When the phage carries the antisense strand the primer is identical to the region of the sense strand that contains the codon to be mutated except for a mismatch with that codon that defines a deletion of the codon or a triplet that codes for another amino acid. When the phage carries the sense strand the primer is complementary to the region of the sense strand that contains the codon to be mutated except for an appropriate mismatch in the triplet that is paired with the codon to be deleted. Conditions that may be used in the hybridization are described by Smith, M. and Gillam, S., supra. The temperature will usually range between about 0° C. and 70° C., more usually about 10° C. to 50° C. After the hybridization, the primer is extended on the phage DNA by reaction with DNA polymerase I, T4 DNA polymerase, reverse transcriptase or other suitable DNA polymerase. The resulting dsDNA is converted to closed circular dsDNA by treatment with a DNA ligase such as T4 DNA ligase. DNA molecules containing single-stranded regions may be destroyed by S1 endonuclease treatment.

Oligonucleotide-directed mutagenesis may be similarly employed to make a mutant IL-2 gene that encodes a mutein having IL-2 activity but having cys 125 changed to serine 125. The preferred oligonucleotide primer used in making this mutant IL-2 gene when the phage carries the sense strand of the gene is GATGATGCTTCTGAGAAAAGGTAATC. This oligonucleotide has a C→G change at the middle base on the triplet that is paired with codon 125 of the IL-2 gene.

The resulting mutational heteroduplex is then used to transform a competent host organism or cell. Replication of the heteroduplex by the host provides progeny from both strands. Following replication the mutant gene may be isolated from progeny of the mutant strand, inserted into an appropriate expression vector, and the vector used to transform a suitable host organism or cell. Preferred vectors are plasmids pBR322, pCR1, and variants thereof, synthetic vectors and the like. Suitable host organisms are E. coli, Pseudomonas, Bacillus subtilis, Bacillus thuringiensis, various strains of yeast, Bacillus thermophilus, animal cells such as mice, rat or Chinese hamster ovary (CHO) cells, plant cells, animal and plant hosts and the like. It must be recognized that when a host of choice is transformed with the vector, appropriate promoter-operator sequences are also introduced in order for the mutein to be expressed. Hosts may be prokaryotic or eukaryotic (processes for inserting DNA into eukaryotic cells are described in PCT applications Nos. US81/00239 and US81/00240 published Sept. 3, 1981). E. coli and CHO cells are the preferred hosts. The muteins obtained in accordance with the present invention may be glycosylated or unglycosylated depending on the glycosylation occurring in the native parent protein and the host organism used to produce the mutein. If desired, unglycosylated mutein obtained when E. coli or a Bacillus is the host organism, may be optionally glycosylated in vitro by chemical, enzymatic and other types of modifications known in the art.

In the preferred embodiment of the subject invention respecting IFN-$\beta$, the cysteine residue at position 17 in the amino acid sequence of IFN-$\beta$, as shown in FIG. 1, is changed to serine by a T→A transition of the first base of codon 17 of the sense strand of the DNA sequence which codes for the mature IFN-$\beta$. The site-specific mutagenesis is induced using a synthetic 17-nucleotide primer GCAATTTTCAGAGTCAG which is identical to a seventeen nucleotide sequence on the sense strand of IFN-$\beta$ in the region of codon 17 except for a single base mismatch at the first base of codon 17. The mismatch is at nucleotide 12 in the primer. It must be recognized that the genetic code is degenerate and that many of the amino acids may be encode by more than one codon. The base code for serine, for example, is six-way degenerate such that the codons, TCT, TCG, TCC, TCA, AGT, and ACG all code for serine. The AGT codon was chosen for the preferred embodiment for convenience. Similarly, threonine is encoded by any one of codons ACT, ACA, ACC and ACG. It is intended that when one codon is specified for a particular amino acid, it includes all degenerate codons which encode that amino acid. The 17-mer is hybridized to single-stranded M13 phage DNA which carries the antisense strand of the IFN-$\beta$ gene. The oligonucleotide primer is then extended on the DNA using DNA polymerase I Klenow fragment and the resulting dsDNA is converted to closed circular DNA with T4 ligase. Replication of the resulting mutational heteroduplex yields clones from the DNA strand containing the mismatch. Mutant clones may be identified and screened by the appearance or disappearance of specific restriction sites, antibiotic resistance or sensitivity, or by other methods known in the art. When cysteine is substituted with serine, the T→A transition, shown in FIG. 2, results in the creation of a new HinfI restriction site in the structural gene. The mutant clone is identified by using the oligonucleotide primer as a probe in a hybridization screening of the mutated phage plaques. The primer will have a single mismatch when hybridized to the parent but will have a perfect match when hybridized to the mutated phage DNA, as indicated in FIG. 2. Hybridization conditions can then be devised where the oligonucleotide primer will preferentially hybridize to the mutated DNA but not to the parent DNA. The newly generated HinfI site also serves as a means of confirming the single base mutation in the IFN-β gene.

The M13 phage DNA carrying the mutated gene is isolated and spliced into an appropriate expression vector, such as plasmid pTrp3, and E. coli strain MM294 is transformed with the vector. Suitable growth media for culturing the transformants and their progeny are known to those skilled in the art. The expressed mutein of IFN-β is isolated, purified and characterized.

The following examples are presented to help in the better understanding of the subject invention and for purposes of illustration only. They are not to be construed as limiting the scope of the invention in any manner. Examples 1-11 describe the preparation of a mutein of IFN-β. Examples 12-20 describe the preparation of a mutein of IL-2.

EXAMPLE 1

Cloning of the IFN-β Gene Into M13 Vector

Figure 3:
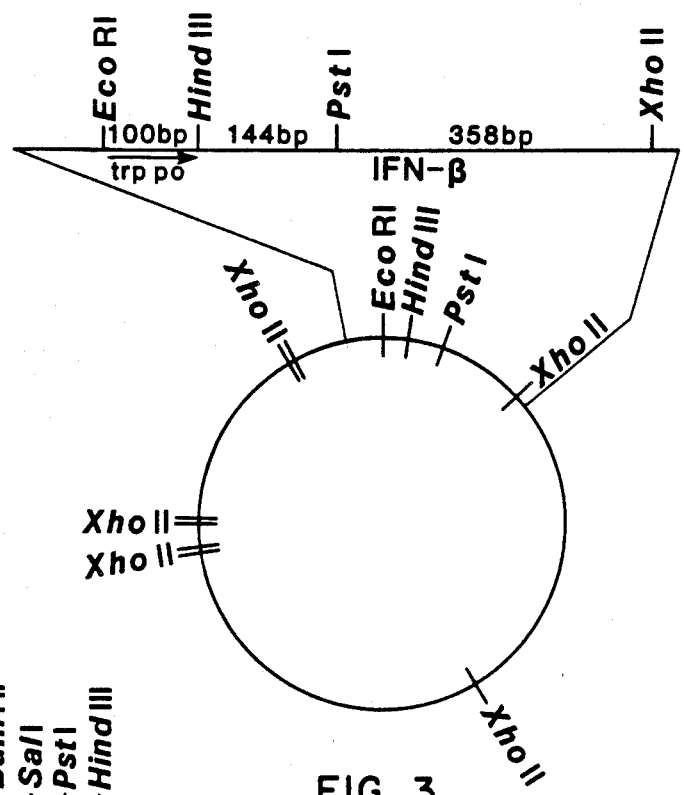
FIG. 3 shows a diagram of plasmid p$\beta$ltrp including the IFN-$\beta$ gene.
Figure 4:
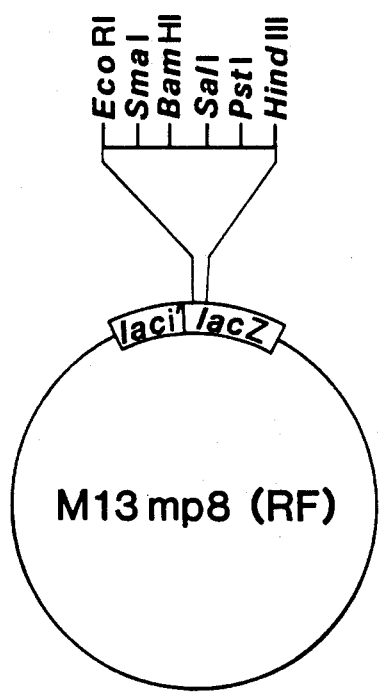
FIG. 4 is a diagram of the cloning vector M13mp8 phage.
Figure 5:
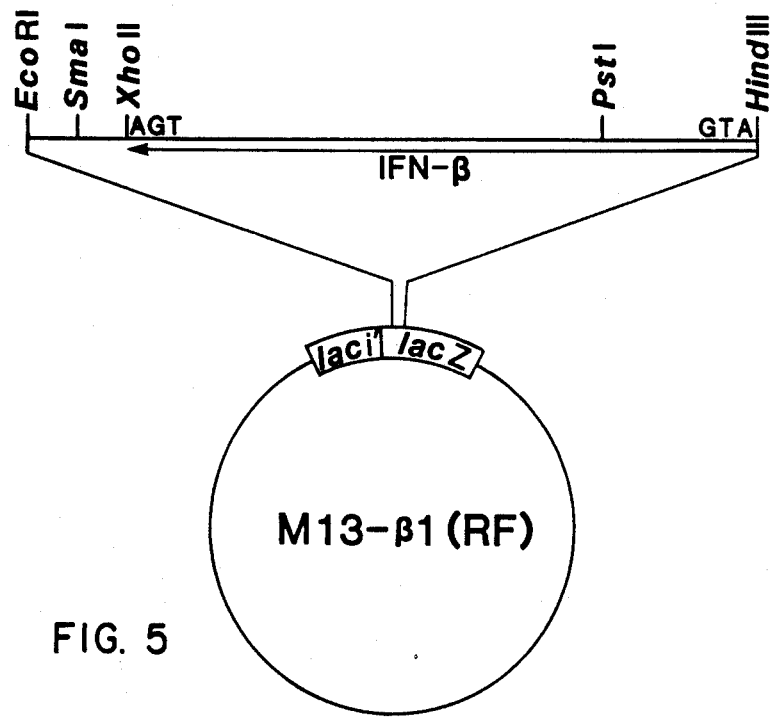
FIG. 5 shows the restriction map of clone M13-$\beta$1.

The use of M13 phage vector as a source of single-stranded DNA template has been demonstrated by G. F. Temple et al, *Nature* (1982) 296: 537-540. Plasmid pβ1trp (FIG. 3) containing the IFN-β gene under control of E. coli trp promoter, was digested with the restriction enzymes HindIII and XhoII. The M13mp8 (J. Messing, "Third Cleveland Sympmosium on Macromolecules: Recombinant DNA," Ed. A. Walton, Elsevier Press, 143-153 (1981)) replicative form (RF) DNA (FIG. 4) was digested with restriction enzymes HindIII and BamHI, and mixed with the pβ1trp DNA which had previously been digested with HindIII and XhoII. The mixture was then ligated with T4 DNA ligase and the ligated DNA transformed into competent cells of E. coli strain JM 103 and plated on Xgal indicator plates (J. Messing, et al, *Nucleic Acids Res* (1981) 9: 309-321). Plaques containing recombinant phage (white plaques) were picked, inoculated into a fresh culture of JM 103 and minipreps of RF molecules prepared from the infected cells (H. D. Birnboim and J. Doly, *Nucleic Acid Res* (1979) 7: 1513-1523). The RF molecules were digested with various restriction enzymes to identify the clones containing the IFN-β insert. The restriction map of one such clone (M13-β1) is shown in FIG. 5. Single-stranded (ss) phage DNA was prepared from clone M13-β1 to serve as a template for site-specific mutagenesis using a synthetic oligonucleotide.

EXAMPLE 2

Site-Specific Mutagenesis

Forty picomoles of the synthetic oligonucleotide GCAATTTTCAGAGTCAG (primer) was treated with T4 kinase in the presence of 0.1 mM adenosine triphosphate (ATP), 50 mM hydroxymethylaminomethane hydrochloride (Tris-HCl) pH 8.0, 10 mM MgCl2, 5 mM dithiothreitol (DTT) and 9 units of T4 kinase, in 50 μl at 37° C. for 1 hr. The kinased primer (12 pmole) was hybridized to 5 μg of ss M13-β1 DNA in 50 μl of a mixture containing 50 mM NaCl, 10 mM Tris-HCl, pH 8.0, 10 mM MgCl2 and 10 mM β-mercaptoethanol, by heating at 67° C. for 5 min and at 42° C. for 25 min. The annealed mixture was then chilled on ice and then added to 50 μl of a reaction mixture containing 0.5 mM each of deoxynucleoside triphosphate (dNTP), 80 mM Tris-HCl, pH 7.4, 8 mM MgCl2, 100 mM NaCl, 9 units of DNA polyerase I, Klenow fragment, 0.5 mM ATP and 2 units of T4 DNA ligase, incubated at 37° C. for 3 hr and at 25° C. for 2 hr. The reaction was then terminated by phenol extraction and ethanol precipitation. The DNA was dissolved in 10 mM Tris-HCl pH 8.0, 10 mM ethylenediaminetetraacetic acid (EDTA), 50% sucrose and 0.05% bromophenylblue and electrophoresed on 0.8% agarose gel in the presence of 2 μg/ml of ethidium bromide. The DNA bands corresponding to the RF forms of M13-β1 were eluted from gel slices by the perchlorate method (R. W. Davis, et al, "Advanced Bacterial Genetics", Cold Spring Harbor Laboratory, N.Y., p. 178-179 (1980)). The eluted DNA was used to transform competent JM 103 cells, grown overnight and ssDNA isolated from the culture supernatant. This ssDNA was used as a template in a second cycle of primer extension, the gel purified RF forms of the DNA were transformed into competent JM 103 cells, plated onto agar plates and incubated overnight to obtain phage plaques.

EXAMPLE 3

Site Specific Mutagenesis

The experiment of Example 2 above is repeated except that the synthetic oligonucleotide primer used is GCAATTTTCAGACTCAG to change codon 17 of the IFN-β gene from one that codes for cysteine to one that codes for threonine.

EXAMPLE 4

Site Specific Deletion

The experiment of Example 2 above is repeated except that the synthetic oligonucleotide primer used is AGCAATTTTCAGCAGAAGCTCCTG to delete codon 17 of the IFN-β gene.

EXAMPLE 5

Screening And Identification of Mutagenized Plaques

Plates containing mutated M13-β1 plaques (Example 1) as well as two plates containing unmutated M13-β1 phage plaques, were chilled to 4° C. and plaques from each plate transferred onto two nitrocellulose filter circles by layering a dry filter on the agar plate for 5 min for the first filter and 15 min for the second filter. The filters were then placed on thick filter papers soaked in 0.2N NaOH, 1.5M NaCl and 0.2% Triton X-100 for 5 min, and neutralized by layering onto filter papers soaked with 0.5M Tris-HCl, pH 7.5 and 1.5M NaCl for another 5 min. The filters were washed in a similar fashion twice on filters soaked in 2×SSC (standard saline citrate), dried and then baked in a vacuum oven at 80° C. for 2 hr. The duplicate filters were prehybridized at 55° C. for 4 hr with 10 ml per filter of DNA hybridization buffer (5×SSC) pH 7.0, 4×Denhardt's solution (polyvinylpyrrolidine, ficoll and bovine serum albumin, 1×=0.02% of each), 0.1% sodium dodecyl sulfate (SDS), 50 mM sodium phosphate buffer pH 7.0 and 100 μg/ml of denatured salmon sperm DNA. $^{32}$P-labeled probe was prepared by kinasing the oligonucleotide primer with $^{32}$P-labeled ATP. The filters were hybridized to 3.5×10[5] cpm/ml of $^{32}$P-labeled primer in 5 ml per filter of DNA hybridization buffer at 55° C. for 24 hr. The filters were washed at 55° C. for 30 min each in washing buffers containing 0.1% SDS and decreasing amounts of SSC. The filters were washed initially with buffer containing 2×SSC and the control filters containing unmutated M13-β1 plaques were checked for the presence of any radioactivity using a Geiger counter. The concentration of SSC was lowered stepwise and the filters washed until no detectable radioactivity remained on the control filters with the unmutated M13-β1 plaques. The lowest concentration of SSC used was 0.1×SSC. The filters were air dried and autoradiographed at −70° C. for 2–3 days. 480 plaques of mutated M13-β1 and 100 unmutated control plaques were screened with the kinased oligonucleotide probe. None of the control plaques hybridized with the probe while 5 mutated M13-β1 plaques hybridized with the probe.

Figure 6:
FIG. 6 shows the sequencing gel pattern of the mutant IFN-$\beta_{ser17}$ gene showing a single base change in the coding region.

One of the five mutated M13-β1 plaques (M13-SY2501) was picked and inoculated into a culture of JM 103. ssDNA was prepared from the supernatant and double-stranded (ds) DNA was prepared from the cell pellet. The ssDNA was used as a template for the dideoxy-sequencing of the clone using the M13 universal primer. The result of the sequence analysis is shown in FIG. 6, confirming that the TGT cys codon has been converted to an AGT ser codon.

EXAMPLE 6

Expression of Mutated IFN-β in *E. coli*

Figure 7:
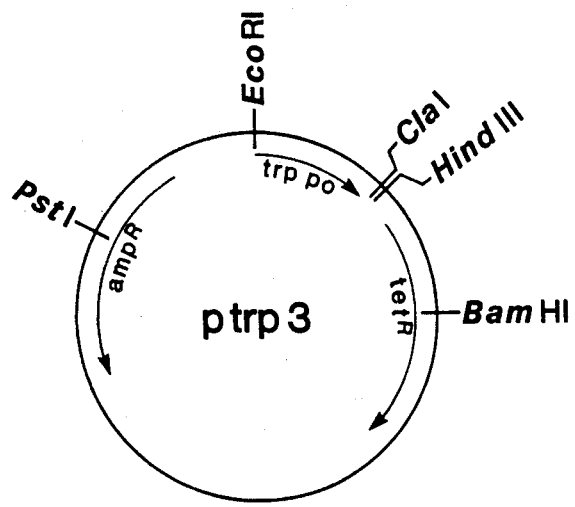
FIG. 7 is a diagramn of the expression plasmid pTrp3.
Figure 9:
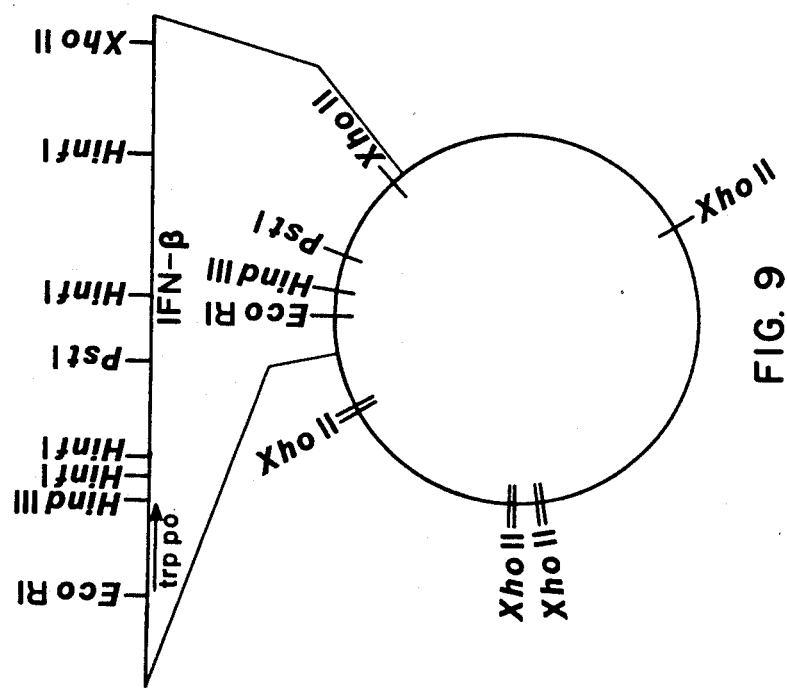
FIG. 9 is a restriction map of clone pSY2501.

RF DNA from M13-SY2501 was digested with restriction enzymes HindIII and XhoII and the 520 bp insert fragment purified on a 1% agarose gel. The plasmid pTrp3 containing the *E. coli* trp promoter (FIG. 7) was digested with the enzymes HindIII and BamHI, mixed with the purified M13-SY2501 DNA fragment, and ligated in the presence of T4 DNA ligase. The ligated DNA was transformed into *E. coli* strain MM294. Ampicillin resistant transformants were screened for sensitivity to the drug tetracycline. Plasmid DNA from five ampicillin resistant, tetracylcine sensitive clones were digested with Hinfl to screen for the presence of the M13-SY2501 insert. FIG. 8a shows the HINfI restriction pattern of one of the clones (pSY2501), comparing it with the HinfI pattern of the original IFN-β clone, pβ1trp. As expected, there is an additional HinfI site in pSY2501, cleaving the 197 bp IFN-β internal fragment to a 169 bp fragment and a 28 fragment (FIG. 8b). A restriction map of the clone pSY2501 is shown in FIG. 9. The complete DNA sequence of the mutant IFN-β gene is shown in FIG. 10 together with the predicted amino acid sequence.

The plasmid designated as clone pSY2501 was deposited with the Agricultural Research Culture Collection (NRRL), Fermentation Laboratory, Northern Regional Research Center, Science and Education Administration, U.S. Department of Agriculture, 1815 North University Street, Peoria, Ill. 60604 on Mar. 30, 1983 and was assigned accession numbers CMCC No. 1533 and NRRL No. B-15356.

Cultures of pSY2501 and pβ1trp, which include progeny thereof, were grown up to an optical density (OD$_{600}$) of 1.0. Cell free extracts were prepared and the amount of IFN-β antiviral activity assayed on GM2767 cells in a microtiter assay. Extracts of clone pSY2501 exhibited three to ten times higher activity than pβ1trp (Table I), indicating that clone pSY2501 was either synthesizing more protein exhibiting IFN-β activity or that the protein made had a higher specific activity.

TABLE I

| EXTRACT | ANTIVIRAL ACTIVITY (U/ml) |
|---|---|
| pSY2501 | $6 \times 10^5$ |
| pβ1trp | $1 \times 10^5$ |
| ptrp3 (control) | 30 |

Figure 11:
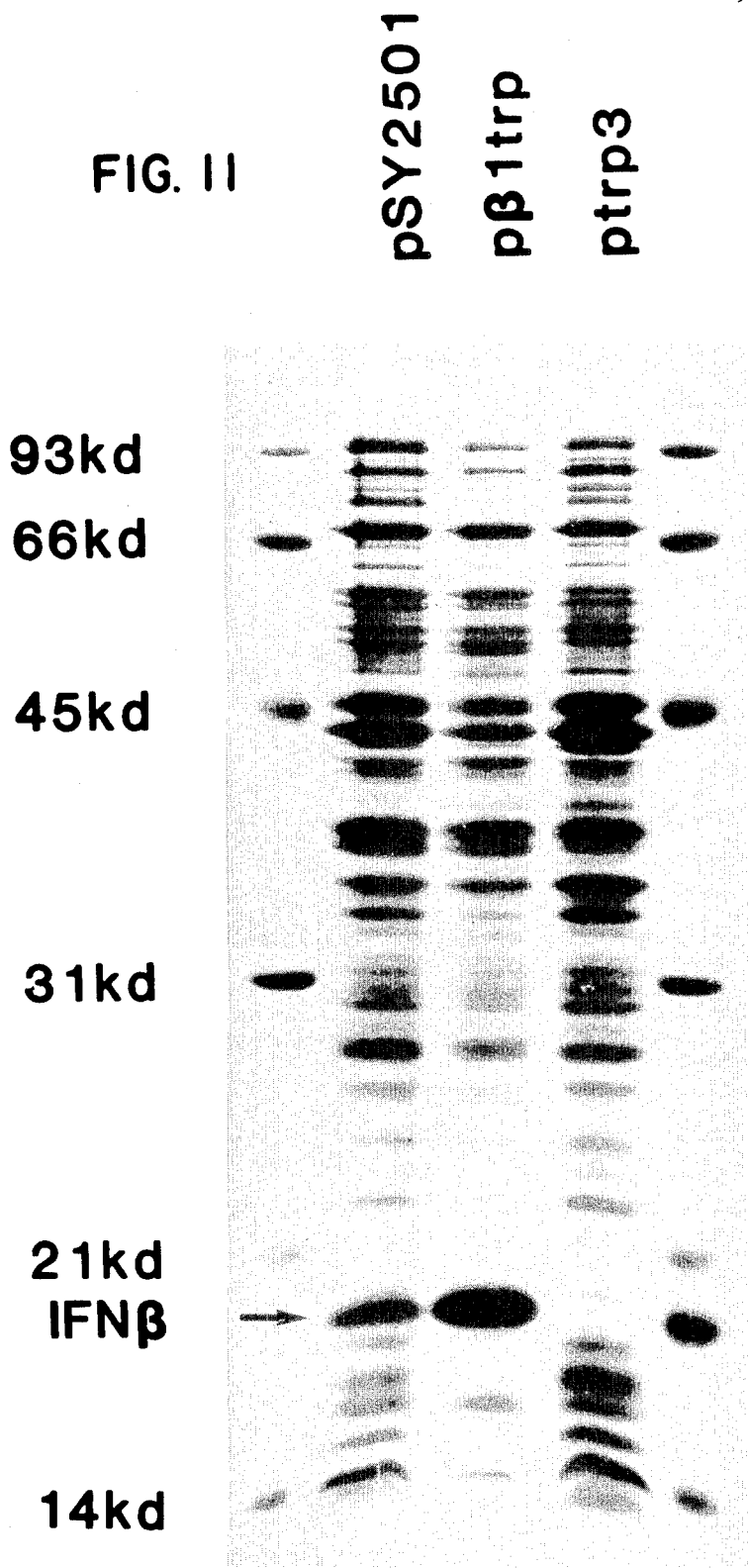
FIG. 11 shows the single 18,000 dalton protein band corresponding to IFN-$\beta_{ser17}$ in the extracts of clones pSY2501 and p$\beta$1trp.

In order to determine if clone pSY2501 was synthesizing several times more active protein, the extracts of both clones were electrophoresed on a SDS polyacrylamide gel together with a control extract and the gel stained with coomasie blue to visualize the proteins. As shown in FIG. 11, there was only one protein band corresponding to an apparent 18,000 dalton protein that was present in the extracts of clones pSY2501 and pβ1trp but not in the control extract of ptrp3. This protein, which has a molecular weight of about 20,000 daltons but shows a gel migration pattern of an 18,000 dalton protein was previously shown to be IFN-β by purification of this protein from extracts of pβ1trp. Since there is less of this protein in extracts of pSY2501 than in extracts of pβ1trp, the specific activity of the protein in extracts of clone pSY2501 was higher than that of clone pβ1trp.

EXAMPLE 7

The plasmid pSY2501 was transformed into a competent subvariant of *E. coli* strain MM294, designated MM294-1. A sample of the resulting transformant was deposited in the American Type Culture Collection 12301 Parklawn Drive, Rockville, Md. 20852 USA on Nov. 18, 1983 under ATCC number 39,517.

EXAMPLE 8

Production of IFN-β$_{ser17}$

IFN-β$_{ser17}$ was recovered from *E. coli* that had been transformed to produce IFN-β$_{ser17}$. The *E. coli* were grown in the following growth medium to an OD of 10–11 at 680 nm (dry wt 8.4 g/l).

| Ingredient | Concentration |
|---|---|
| NH$_4$Cl | 20 mM |
| K$_2$SO$_4$ | 16.1 mM |
| KH$_2$PO$_4$ | 7.8 mM |
| Na$_2$HPO$_4$ | 12.2 mM |
| MgSO$_4$.7H$_2$O | 3 mM |
| Na$_3$ citrate.2H$_2$O | 1.5 mM |
| MnSO$_4$.4H$_2$O | 30 μM |
| ZnSO$_4$.7H$_2$O | 30 μM |
| CuSO$_4$.5H$_5$O | 3 μM |
| L-Tryptophan | 70 mg/l |
| FeSO$_4$.7H$_2$O | 72 μM |
| thiamine.HCl | 20 mg/l |
| glucose | 40 g/l |

15 pH control with NH$_4$OH

A 9.9 l (9.9 kg) harvest of the transformed *E. coli* was cooled to 20° C. and concentrated by passing the harvest through a cross-flow filter at an average pressure drop of ~110 kpa and steady-state filtrate flow rate of 260 ml/min until the filtrate weight was 8.8 kg. The concentrate (approximately one liter) was drained into a vessel and cooled to 15° C. The cells in the concentrate were then disrupted by passing the concentrate through a Manton-Gaulin homogenizer at 5° C., ~69,000 kpa. The homogenizer was washed with one liter phosphate buffered saline, pH 7.4 (PBS), and the wash was added to the disruptate to give a final volume of two liters. This volume was continuously centrifuged at 12000×g at a 50 ml/min flow rate. The solid was separated from the supernatant and resuspended in four liters PBS containing 2% by wt SDS. This suspension was stirred at room temperature for 15 min after which there was no visible suspended material. The solution was then extracted with 2-butanol at a 1:1 2-butanol:solution volume ratio. The extraction was carried out in a liquid-liquid phase separator using a flow rate of 200 ml/min. The organic phase was then separated and evaporated to dryness to yield 21.3 g of protein. This was resuspended in distilled water at a 1:10 volume ratio.

The recovered product was assayed for human IFN-$\beta$ activity using an assay based on protection against viral cytopathic effect (CPE). The assay was made in microtiter plates. Fifty $\mu$l of minimum essential medium were charged into each well and 25 $\mu$l of the sample was placed in the first well and 1:3 volume dilutions were made serially into the following wells. Virus (*vesicular stomatitis*), cell (human fibroblast line GM-2767), and reference IFN-$\beta$ controls were included on each plate. The reference IFN-$\beta$ used was 100 units per mol. The plates were then irradiated with UV light for 10 min. After irradiation 100 $\mu$l of the cell suspension ($1.2 \times 10^5$ cells/ml) was added to each well and the trays were incubated for 18-24 hr. A virus solution at one plaque-forming unit per cell was added to each well except the cell control. The trays were then incubated until the virus control showed 100% CPE. This normally occurred 18-24 hr after adding the virus solution. Assay results were interpreted in relation to the location of the 50% CPE well of the reference IFN-$\beta$ control. From this point the titer of interferon for all samples on the plate was determined. The specific activity of the recovered product was determined to be $5 \times 10^7$ U/mg.

EXAMPLE 9

Acid Precipitation And Chromatographic Purification

The process of Example 8 was repeated except that after extraction and separation of the aqueous and organic phases and mixing of the organic phase with PBS at a volume ratio of 3:1 the pH of the mixture was lowered to about 5 by addition of glacial acetic acid. The resulting precipitate was separated by centrifugation at 10,000-17,000$\times$g for 15 min and the pellet was redissolved in 10% w/v SDS, 10 mM DTT, 50 mM sodium acetate buffer, pH 5.5, and heated to 80° C. for 5 min.

The solution was then applied to a Brownlee RP-300, 10 $\mu$M, "Aquapore" column using a Beckman gradient system. Buffer A was 0.1% trifluoroacetic acid (TFA) in H$_2$O; buffer B was 0.1% TFA in acetonitrile. Detection was by ultraviolet absorbance at 280 nm. The solvent program was linear gradient of 0% buffer B to 100% buffer B in three hr. Fractions containing highest interferon activities were pooled and the specific activity of the pooled interferon preparation was determined to be $9.0 \times 10^7$ to $3.8 \times 10^8$ international units per mg protein, as compared to about $2 \times 10^8$ U/mg for native IFN-$\beta$.

EXAMPLE 10

Biochemical Characterization of IFN-$\beta$ Ser$_{17}$

Amino acid compositions were determined after 24-72 hr timed hydrolysis of 40 $\mu$g samples of IFN in 200 $\mu$l of 5.7N HCl, 0.1% phenol, at 108° C. Proline and cysteine were determined in the same fashion after performic acid oxidation; in this case, phenol was omitted from the hydrolysis. Tryptophan was analyzed after 24 hr hydrolysis of 400 $\mu$l samples in 5.7N HCl, 10% mercaptoacetic acid (no phenol). Analysis was performed on a Beckman 121MB amino acid analyzer using a single column of AA10 resin.

The amino acid composition calculated from representative 24-, 48-, 72-hr acid hydrolyses of purified IFN-$\beta$ Ser$_{17}$ agrees well with that predicted by the DNA sequence of the cloned IFN gene, minus the missing N-terminal methionine.

The amino acid sequence of the first 58 residues from the amino acid terminus of purified IFN was determined on a 0.7 mg sample in a Beckman 890C sequanator with 0.1M Quadrol buffer. PTH amino acids were determined by reverse-phase HPLC on an Altex ultrasphere ODS column (4.6$\times$250 mm) at 45° C. eluted at 1.3 min at 40% buffer B, and 8.4 min from 40-70% buffer B, where buffer A was 0.0115M sodium acetate, 5% tetrahydrofuran (THF), pH 5.11 and buffer B was 10% THF in acetonitrile.

The N-terminal amino acid sequence of IFN-$\beta$ Ser$_{17}$ determined matches the expected sequence predicted from the DNA sequence, except for the absence of N-terminal methionine.

EXAMPLE 11

Alternative IFN-$\beta_{ser}$ Production and Purification Process

*E. coli* transformed with pSY2501 were grown in the following medium:

| Ingredient | Approximate Initial Concentration |
| --- | --- |
| Na$_3$ Citrate.2H$_2$O | 3 mM |
| KH$_2$PO$_4$ | 30 mM |
| (NH$_4$)$_2$SO$_4$ | 74 mM |
| MgSO$_4$.7H2O | 3 mM |
| MnSO$_4$.H$_2$O | 46 $\mu$M |
| ZnSO$_4$.7H$_2$O | 46 $\mu$M |
| CuSO$_4$.5H$_2$O | 1-2 $\mu$M |
| L-tryptophan | 350 $\mu$M |
| FeSO$_4$.7H2O | 74 $\mu$M |
| thiamine.HCl | 0.002% |
| glucose | 0.5% |

Dow Corning Antifoam polypropylene glycol, 25% solution, glucose, 50% solution, and KOH, 5N, were added on demand.

Temperature was maintained at 37$\pm$1° C., pH at 6.5$\pm$0.1 with NaOH, and dissolved oxygen at 30% of air saturation. Optical density and residual glucose measurements were taken at 14 hr and at approximately one hr intervals thereafter. Harvest was made when glucose consumption reached 40$\pm$6 g/l (OD at 680 nm=10-11).

The harvested material was concentrated approximately 3-fold by circulating it through a microporous cross-flow filter under pressure. The concentrated cells were diafiltered against deionized water until the harvest material was concentrated 4-5 fold. The cells were then disrupted by passing them through a Manton-Gaulion homogenizer at $\sim$4.1-5.5$\times 10^4$ kpa. After the initial pass SDS-sodium phosphate buffer was added to a final concentration of 2% SDS, 0.08M sodium phosphate and homogenization was continued for one hr. Solid DTT was then added to a final concentration of 50 mM and the homogenizate was heated to 90$\pm$5° C. for 10 min. The resulting cell suspension was extracted with 2-butanol at a 1:1 2-butanol:suspension volume ratio in a static mixer. The mixture was then centrifuged and the 2-butanol rich phase was collected.

The 2-butanol rich phase was mixed with 2.5 volumes of 0.1% SDS in PBS. Solid DTT was added to a final concentration of 2 mM. The pH of the mixture was adjusted to 6.2±0.1 with glacial acetic acid and this mixture was centrifuged. The resulting paste was collected and resuspended in PBS +10% SDS with pH adjustment to 8.5±0.1 using 1N NaOH. Solid DTT was added to a final concentration of 100 mM and the suspension was heated to 90±5° C. for 10 min. The suspension was then cooled to ~25° C., the pH was adjusted to 5.5±0.1 with glacial acetic acid, and the solution was filtered.

The solution was then applied to a Sephacryl S-200 pre column and the fractions containing highest interferon activities were pooled and concentrated by ultrafiltration with a 10 Kdal molecular weight cutoff. The concentrate was oxidized by adding equimolar amounts of protein and iodosobenzoic acid into a reaction vessel containing 2 mM sodium pyrophosphate, 0.1% SDS and 1 mM EDTA. The pH was controlled during oxidation at 9.0±0.1 with 0.5N NaoH and adjusted to 5.5±0.2 when oxidation was complete. After oxidation the concentrate was again passed through the ultrafiltration unit with a 10 Kdal molecular weight cutoff.

The concentrate was applied to a main Sephacryl S-200 column and the fractions were analyzed by SDS-PAGE to determine those containing no high molecular weight contaminants. Those fractions were pooled and passed through the ultrafiltration unit. The filtered concentrate was then fractionated on a Sephadex G-75 column. SDS-PAGE analysis of the fractions was made to determine those containing no low or high molecular weight contaminants. Those fractions were pooled for desalting.

A Sephadex G-25 column equilibrated with 1 mM NaOH was loaded with the pooled fractions from the Sephadex G-75 column using distilled water adjusted to pH 10.8-11 with 50% NaOH. The purified product was collected as the void volume peak. This desalted, purified IFN-β mutein may be formulated in known manners for therapeutic administration.

Biological Testing of IFN-$\beta_{ser17}$

Antigenic Comparison

IFN-$\beta_{ser17}$ was compared antigenically to IFN-$\beta$ produced from diploid fibroblasts using virus neutralizing tests. A polyvalent antiserum to the diploid fibroblast IFN-$\beta$ was prepared in rabbits. This antiserum blocked the antiviral activity of both the diploid fibroblast IFN-$\beta$ and the IFN-$\beta_{ser17}$ in the virus neutralization tests, indicating the two proteins are indistinguishable antigenically.

Antiviral Activity

The purified IFN-$\beta_{ser17}$ was compared in its antiviral activity to naturally produced IFN-$\beta$. Inhibition of *vesicular stomatitis* virus replication in diploid foreskin fibroblast (HS27F) was indistinguishable from that of the natural molecule. Similarly, inhibition of herpes simplex virus type 1 in HS27F fibroblasts by the natural and mutant proteins were comparable.

Antiproliferative Activity

The antiproliferation activity of IFN-$\beta_{ser17}$ for continuous cell lines was compared with that of naturally produced IFN-$\beta$. T24 cells derived from a transitional cell carcinoma were treated with 200 units/ml of the proteins. Cell growth was inhibited significantly (p<0.02) by both proteins.

Natural Killer (NK) Cell Stimulation

The ability of IFN-$\beta_{ser17}$ to stimulate NK cell (spontaneous cell mediated cytotoxicity) activity was tested. Ficoll-hypaque separated peripheral human mononuclear cells (PMC) or NK-enriched lymphocyte preparations (depleted of monocytes by plastic adherence and of OKT3-positive T cells by treatment with OKT3 antibody plus complement) were incubated overnight in growth medium containing various concentrations of IFN-$\beta_{ser17}$. $^{51}$Cr-labeled target cells were incubated with the effector cells (effector cell:target cell ratio=50:1) for 2-4 hours. NK cell cytoxicity was determined by measuring the amount of label released into the medium. The results of these tests are reported in Table I below.

TABLE I

| | | NK Cell Cytotoxicity by Interferon (specific % $^{51}$Cr release ± SEM) | | | | | |
| | | IFN (units/ml) | | | | | |
| Target Cell | Effector Cells | 0 | 10 | 30 | 100 | 300 | 1000 |
| --- | --- | --- | --- | --- | --- | --- | --- |
| T24 | PMC | 7.23 ± 5.1 | 23.1 ± 4.4 | 24.4 ± 1.1 | 34.1 ± 2.5 | 50.0 ± 2.0 | 40.4 ± 4.4 |
| Chang | PMC | 4.7 ± 0.5 | 7.2 ± 0.8 | 9.5 ± 1.7 | 15.9 ± 1.3 | 21.9 ± 1.4 | 26.9 ± 1.8 |
| Chang | NK Enr | 19.2 ± 4.6 | 39.4 ± 4.1 | ND | 54.2 ± 6.1 | ND | 41.7 ± 5.5 |
| K562 | NK Enr | 41.0 ± 4.6 | 48.4 ± 3.6 | ND | 62.2 ± 3.5 | ND | 63.2 ± 3.5 |

As shown the target cells were killed more effectively by the IFN-$\beta_{ser17}$-treated cells than by the untreated cells.

Clinical Trials

Phase I clinical trials to verify the safety of IFN-$\beta_{ser17}$ in humans have been initiated. These trials involve administering the protein to patients intramuscularly and intravenously at doses ranging between 1×10$^5$ units (1 μg of protein) to 400×10$^6$ units. In initial phase I clinical trials no unexpected adverse effects have occurred.

As indicated above, the IFN-$\beta_{ser17}$ preparation exhibits specific activity levels very close to or better than that of native IFN-$\beta$. IFN-$\beta_{ser17}$ has no free sulfhydryl groups but indicates one —S—S— bond between the only remaining cysteines at positions 31 and 141. The protein does not readily form oligomers and appears to be substantially in the monomeric form. The IFN-$\beta_{ser17}$ obtained in accordance with this invention may be formulated either as a single product or mixtures of the various forms, into pharmaceutically acceptable preparations in inert, nontoxic, nonallergenic, physiologically compatible carrier media for clinical and therapeutic uses in cancer therapy or in conditions where interferon therapy is indicated and for viral infections such as herpes simplex virus I and II, hepatitis B virus, common cold viruses, and rhinovirus. Such media include but are not limited to distilled water, physiological saline, Ringer's solution, Hank's solution and the like. Other non-toxic stabilizing and solubilizing additives such as dextrose, HSA (human serum albumin) and the like may be optionally included. The therapeutic formulations may be administered orally or parenterally such as intravenous, intramuscular, intraperitoneal and subcutaneous administrations. Preparations of the modified IFN-β of the present invention may also be used for topical application in appropriate media normally utilized for such purposes. The IFN-β mutein may be administered either locally or systemically by itself or in combination or conjunction with other therapeutic agents such as acyclovir for prophylactic or therapeutic purposes for example, U.S. Pat. No. 4,355,032. The dose of mutein administered to human patients will depend on whether it is administered continuously (including intermittant) or as a bolus. The amounts administered continuously will typically be lower than the amounts administered as a bolus. The amount will usually be in the range of about $1 \times 5^4$ to $4 \times 10^8$ units, more usually about $1 \times 10^6$ to $1 \times 10^7$ units.

The principal advantages of the above described mutein of IFN-β lie in the elimination of a free sulfhydryl group at position 17 in IFN-β, thereby forcing the protein to form correct disulfide links between cys 31 and cys 141 and to assume the conformation ostensibly required for full biological activity. The increased specific activity of the IFN-$β_{ser17}$ enables the use of smaller dosages in therapeutic uses. By deleting the free —SH group, the IFN-$β_{ser17}$ protein does not form dimers and oligomers so readily as the microbially produced IFN-β. This facilitates purification of the protein and enhances its stability.

EXAMPLE 12

The nucleotide sequence for a cDNA clone coding for human IL-2, procedures for preparing IL-2 cDNA libraries, and screening same for IL-2 are described by Taniguchi, T., et al, *Nature* (1983) Vol 24, p 305 et seq.

cDNA libraries enriched in potential IL-2 cDNA clones were made from an IL-2 enriched mRNA fraction obtained from induced peripheral blood lymphocytes (PBL) and Jurkat cells by conventional procedures. The enrichment of the mRNA for IL-2 message was made by fractionating the mRNA and identifying the fraction having IL-2 mRNA activity by injecting the fractions in *Xenopus laevis* oocytes and assaying the oocyte lysates for IL-2 activity on HT-2 cells (J. Watson, *J. Exp Med* (1979) 150: 1570–1519 and S. Gillis et al, *J Immun* (1978) 120: 2027–2032.)

EXAMPLE 13

Screening and Identification of IL-2 cDNA Clones

The IL-2 cDNA libraries were screened using the colony hybridization procedure. Each microtiter plate was replicated onto duplicate nitrocellulose filter papers (S & S type BA-85) and colonies were allowed to grow at 37° C. for 14–16 hr on L agar containing 50 μg/ml ampicillin. The colonies were lysed and DNA fixed to the filter by sequential treatment for 5 min with 500 mM NaOH, 1.5M NaCl, washed twice for 5 min each time with 5×standard saline citrate (SSC). Filters were air dried and baked at 80° C. for 2 hr. The duplicate filters were pre-hybridized at 42° C. for 6–8 hr with 10 ml per filter of DNA hybridization buffer (50% formamide, 5×SSC, pH 7.0, 5×Denhardt's solution (polyvinylpyrrolidine, plus ficoll and bovine serum albumin; 1× =0.2% of each), 50 mM sodium phosphate buffer at pH 7.0, 0.2% SDS, 20 μg/ml Poly U, and 50 μg/ml denatured salmon sperm DNA.

A $^{32}$P-labeled 20-mer oligonucleotide probe was prepared based on the IL-2 gene sequence reported by Taniguchi, T., et al, supra. The nucleotide sequence of the probe was GTGGCCTTCTTGGGCATGTA.

The samples were hybridized at 42° C. for 24–36 hr with 5 ml/filter of DNA hybridization buffer containing the $^{32}$P nucleotide probe. The filters were washed two times for 30 min each time at 50° C. with 2×SSC, 0.1% SDS, then washed twice with 1×SSC and 0.1% SDS at 50° C. for 90 min, air dried, and autoradiographed at −70° C. for 2 to 3 days. Positive clones were identified and rescreened with the probe. Full length clones were identified and confirmed by restriction enzyme mapping and comparison with the sequence of the IL-2 cDNA clone reported by Taniguchi, T., et al, supra.

EXAMPLE 14

Cloning of Il-2 Gene into M13 Vector

Figure 12:
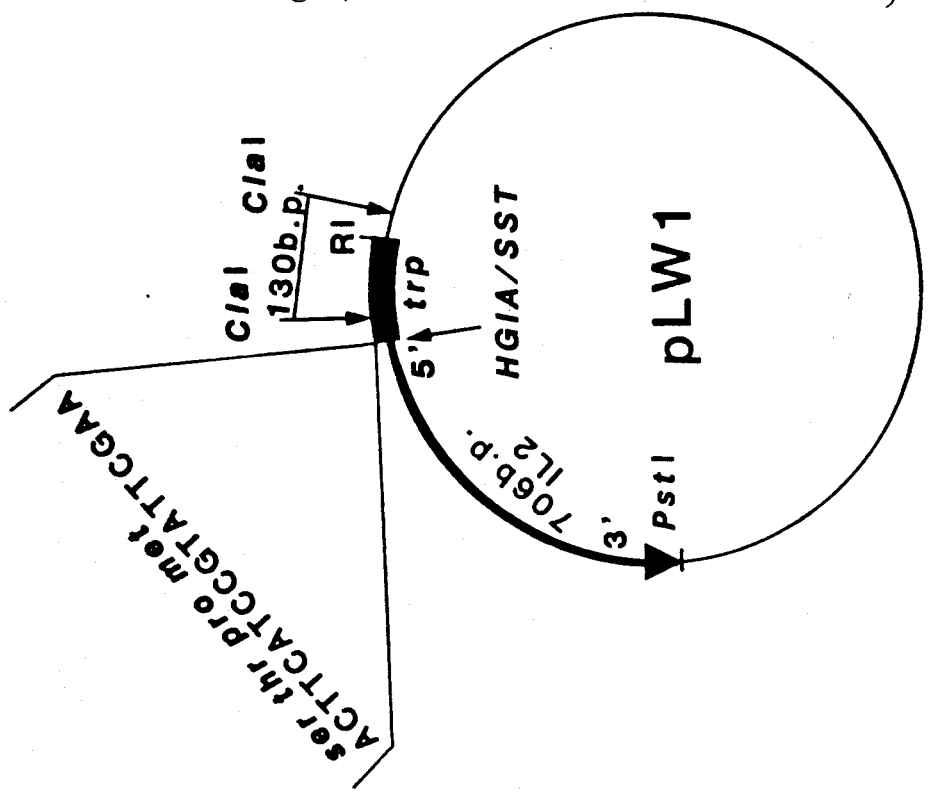
FIG. 12 is a diagram of the plasmid pLW1 which contains the human interleukin-2 (IL-2) gene under the control of the $E$ .$coli$ trp promoter.
Figure 13:
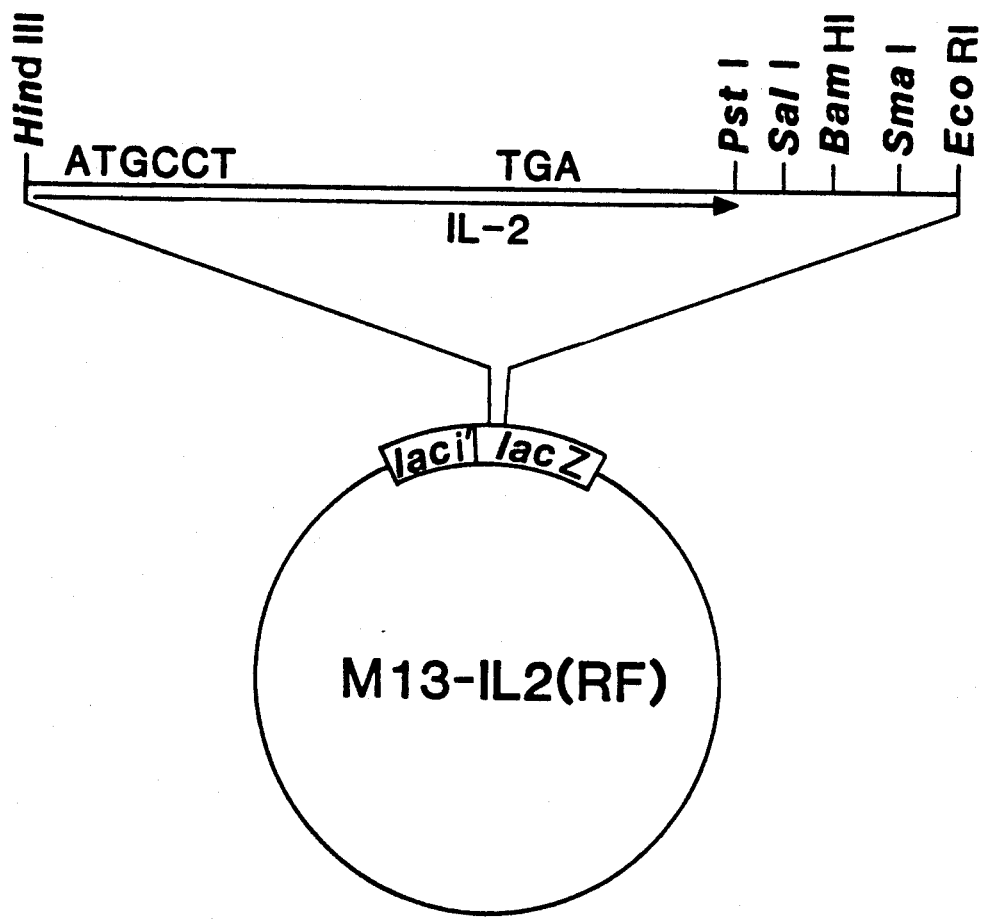
FIG. 13 is a restriction map of phage clone M13-IL2.

The IL-2 gene was cloned into M13mp9 as described in Example 1 using the plasmid pLW1 (FIG. 12) containing the IL-2 gene under the control of the *E. coli* trp promoter. A sample of pLW1 was deposited in the American Type Culture Collection, 12301 Parklawn Drive, Rockville, Md. 20852, USA, on 4 Aug. 1983 and has been assigned ATCC number 39,405. The restriction map of one clone (designated M13-IL2) containing the IL-2 insert is shown in FIG. 13. Single-stranded phage DNA was prepared from clone M13-IL2 to serve as a template for oligonucleotide-directed mutagenesis.

EXAMPLE 15

Oligonucleotide-directed Mutagenesis

As indicated previously, IL-2 contains cysteine residues at amino acid positions 58, 105 and 125. Based on the nucleotide sequences of the portions of the IL-2 gene that contain the codons for these three cysteine residues three oligonucleotide primers were designed and synthesized for mutating the codons for these residues to codons for serine. These oligonucleotides have the following sequences.

CTTCTAGAGACTGCAGATGTTTC (DM27) to change cys 58,
CATCAGCATACTCAGACATGAATG (DM28) to change cys 105 and
GATGATGCTCTGAGAAAAGGTAATC (DM29) to change cys 125.

Forty picomoles of each oligonucleotide were kinased separately in the presence of 0.1 mM ATP, 50 mM Tris-HCl, pH 8.0, 10 mM MgCl$_2$, 5 mM DTT and 9 units of T$_4$ kinase in 50 μl at 37° C. for 1 hr. Each of the kinased primers (10 pmoles) was hybridized to 2.6 μg of ss M13-IL2 DNA in 15 μl of a mixture containing 100 mM NaCl, 20 mM Tris-HCl, pH 7.9, 20 mM MgCl$_2$ and 20 mM β-mercaptoethanol, by heating at 67° C. for 5 min and 42° C. for 25 min. The annealed mixtures were chilled on ice and then adjusted to a final column of 25 μl of a reaction mixture containing 0.5 mM of each dNTP, 17 mM Tris-HCl, pH 7.9, 17 mM MgCl$_2$, 83 mM NaCl, 17 mM β-mercaptoethanol, 5 units of DNA polymerase I Klenow fragment, 0.5 mM ATP and 2 units of T4 DNA ligase, incubated at 37° C. for 5 hr. The reactions were terminated by heating to 80° C. and the reaction mixtures used to transform competent JM103 cells, plated onto agar plates and incubated overnight to obtain phage plaques.

EXAMPLE 16

Screening and Identification of Mutagenized Phage Plaques

Plates containing mutagenized M13-IL2 plaques as well as 2 plates containing unmutagenized M13-IL2 phage plaques, were chilled to 4° C. and phage plaques from each plate were transferred onto two nitrocellulose filter circles by layering a dry filter on the agar plate for 5 min for the first filter and 15 min for the second filter. The filters were then placed on thick filter papers soaked in 0.2N NaOH, 1.5M NaCl and 0.2% Triton for 5 min, and neutralized by layering onto filter papers soaked with 0.5M Tris-HCl, pH 7.5, and 1.5M NaCl for another 5 min. The filters were washed in a similar fashion twice on filters soaked in 2×SSC, dried and then baked in a vacuum oven at 80° C. for 2 hr. The duplicate filters were pre-hybridized at 42° C. for 4 hr with 10 ml per filter of DNA hybridization buffer (5×SSC, pH 7.0, 4×Denhardts solution (polyvinylpyrrolidone, ficoll and bovine serum albumin, 1×=0.02% of each), 0.1% SDS, 50 mM sodium phosphate buffer, pH 7.0 and 100 µg/ml of denatured salmon sperm DNA. $^{32}$P-labelled probes were prepared by kinasing the oligonucleotide primers with labelled ATP. The filters were hybridized to $0.1 \times 10^5$ cpm/ml of $^{32}$P-labelled primers in 5 ml per filter of DNA hybridization buffer at 42° C. for 8 hr. The filters were washed twice at 50° C. for 30 min each in washing buffers containing 0.1% SDS and 2×SSC, and twice at 50° C. for 30 min each with 0.1% SDS and 0.2×SSC. The filters were air dried and autoradiographed at −70° C. for 2-3 days.

Since the oligonucleotide primers DM28 and DM29 were designed to create a new DdeI restriction site in the mutagenized clones (FIG. 14), RF-DNA from a number of the clones which hybridized with each of these kinased primers were digested with the restriction enzyme DdeI. One of the mutagenized M13-IL2 placques which hybridized with the primer DM28 and has a new DdeI restriction site (M13-LW44) was picked and inoculated into a culture of JM103, ssDNA was prepared from the culture supernatant and dsRF-DNA was prepared from the cell pellet. Similarly, a plaque which hybridized with primer DM29 was picked (M13-LW46) and ssDNA and RF-DNA prepared from it. The oligonucleotide primer DM27 was designed to create a new PstI restriction site instead of a DdeI site. Therefore, the plaques that hybridized to this primer were screened for the presence of a new PstI site. One such phage plaque was identified (M13-LW42) and ssDNA and RF-DNA prepared from it. The DNA from all three of these clones were sequenced to confirm that the target TGT codons for cysteine had been converted to a TCT codon for serine.

EXAMPLE 17

Recloning of the Mutagenized IL-2 Gene for Expression in E. coli

Figure 14:
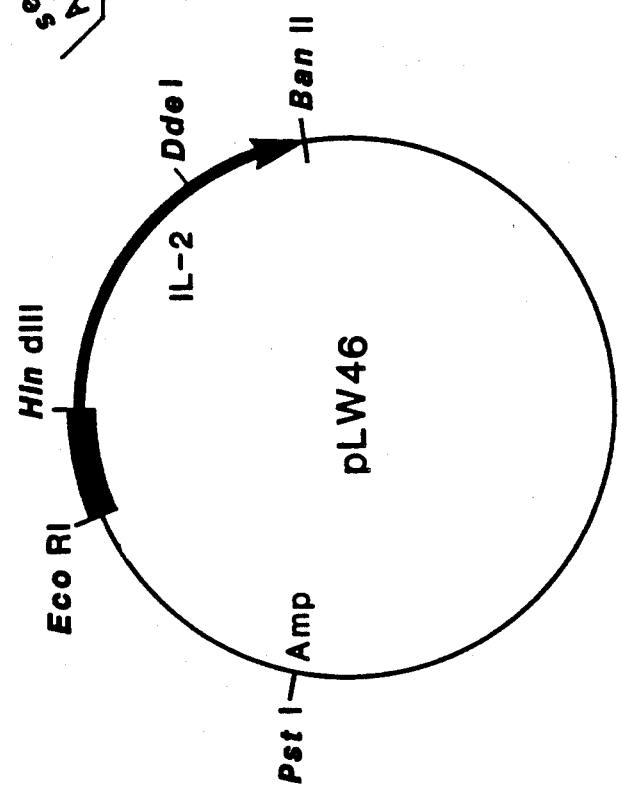
FIG. 14 is a restriction map of the plasmid pLW46.

RF-DNA from M13-LW42, M13-LW44 and M13-LW46 were each digested with restriction enzymes HindIII and BanII and the insert fragments purified from a 1% agarose gel. Similarly, the plasmid pTrp3 (FIG. 7) was digested with HindIII and BanII, the large plasmid fragment containing the trp promoter was purified on an agarose gel and then ligated with each of the insert fragments isolated from M13-LW42, M13-LW44 and M13-LW46. The ligated plasmids were transformed into competent E. coli K12 strain MM294. The plasmid DNAs from these transformants were analyzed by restriction enzyme mapping to confirm the presence of the plasmids pLW42, pLW44 and pLW46. FIG. 14 is a restriction map of pLW46. When each of these individual clones were grown in the absence of tryptophane to induce the trp promoter and cell free extracts analyzed on SDS-polyacrylamide gels, all three clones, pLW42, pLW44 and pLW46, were shown to synthesize a 14.5 kd protein similar to that found in the positive control, pLW21, which has been demonstrated to synthesize a 14.4 kd IL-2 protein. When these same extracts were subjected to assay for IL-2 activity on mouse HT-2 cells, only clones pLW21 (positive control) and pLW46 had significant amounts of IL-2 activity (Table II below), indicating that cys 58 and cys 105 are necessary for biological activity and changing them to serines (pLW42 and pLW44 respectively) resulted in the loss of biological activity. Cys 125 on the other hand must not be necessary for biological activity because changing it to ser 125 (pLW46) did not affect the biological activity.

TABLE II

| Clones | IL-2 Activity (µ/ml) |
|---|---|
| pIL2-7 (negative control) | 1 |
| pLW21 (positive control) | 113,000 |
| pLW42 | 660 |
| pLW44 | 1,990 |
| pLW46 | 123,000 |

FIG. 15a shows the nucleotide sequence of the coding strand of clone pLW46. As compared to the coding strand of the native human IL-2 gene clone pLW46 has a single base change of G→C at nucleotide 374. FIG. 15b shows the corresponding amino acid sequence of the IL-2 mutein encoded by pLW46. This mutein is designated des-alanyl (ala) IL-2$_{ser125}$ As compared to native IL-2 the mutein has a serine instead of a cysteine at position 125, has an initial N-terminal methionine (which is processed off), and lacks the initial N-terminal alanine of the native molecule.

A sample of E. coli K12 strain MM294 transformed with pLW46 was deposited in the American Type Culture Collection, 12301 Parklawn Drive, Rockville, Md. 20852, USA on 26 Sept. 1983 and has been assigned ATCC Number 39,452.

Examples 18 and 19 describe the preparation of an alternative and preferred vector for expressing alanyl (ala) IL-2$_{ser125}$.

EXAMPLE 18

Construction of Ala-IL-2 Expression Vector pLW32

Figure 16:
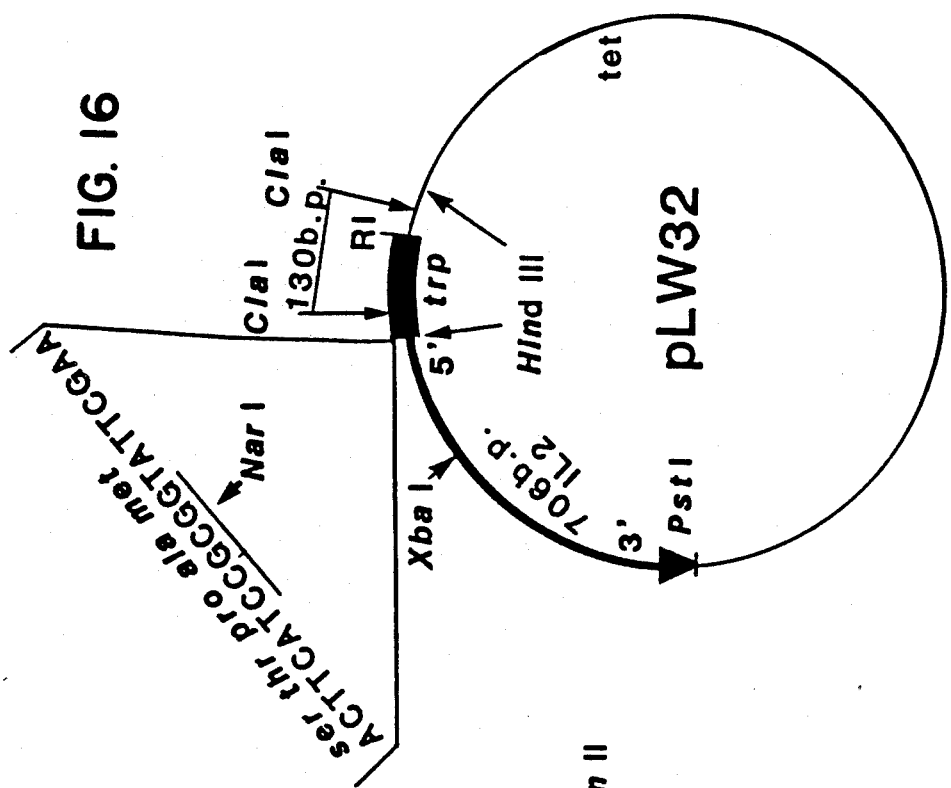
FIG. 16 is a diagram of the plasmid pLW32.

A codon (GCG) for alanine was inserted immediately after the initiation codon of the IL-2 gene of pLW1 by oligonucelotide-directed mutagenesis as follows. The oligonucleotide primer, 5'-GAAGTAGGCG-CCATAAG-3', was kinased, hybridized to ssM13-IL2 DNA, and extended using the general procedure of Example 15 to form a mutational heteroduplex. In addition to the insertion of the GCG codon, the mutagenesis generated a new NarI restriction site in the gene. The heteroduplex was converted to closed circular heteroduplex and the circular heteroduplexes were used to transform competent JM103 cells and plated onto agar plates and incubated as in Example 15. The plates were screened to identify mutagenized M13-IL2 by the procedure of Example 16. One mutagenized phage, identified as M13-LW32, was selected for use in additional cloning and RF-DNA was prepared from it. FIG. 16 is a diagram of plasmid pLW32.

EXAMPLE 19

Construction of Ala-IL-2$_{ser125}$ Expressing Clone pLW55

Figure 17:
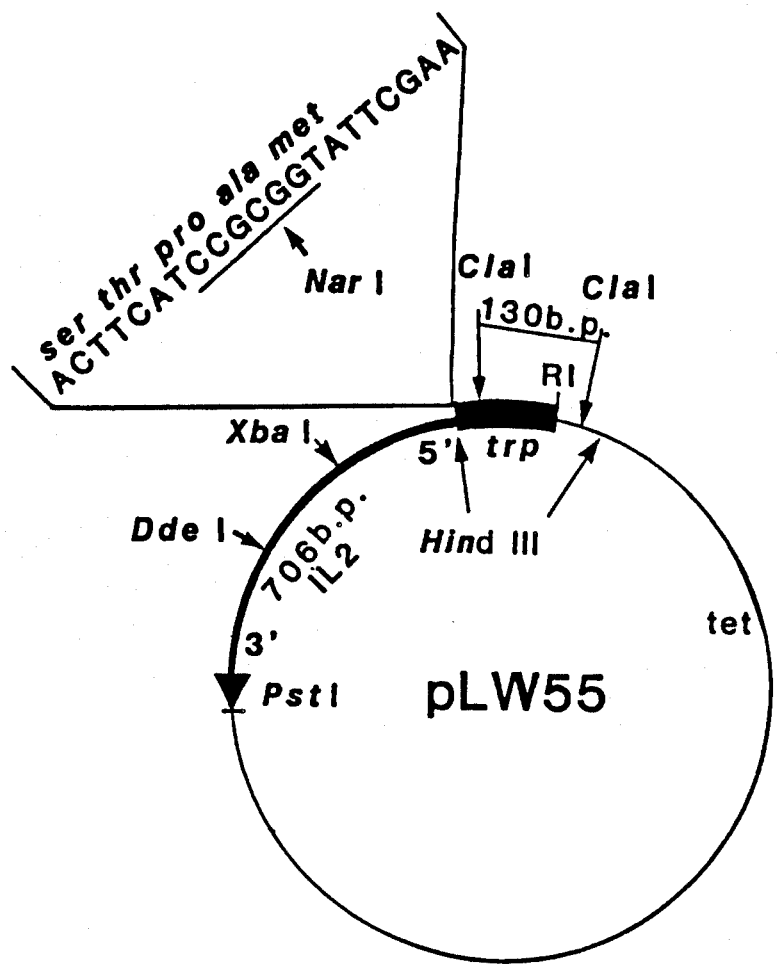
FIG. 17 is a diagram of the plasmid pLW55.

RF-DNA from M13-LW46 (Examples 16 and 17) was digested with XbaI and PstI and the 530 bp fragment containing the carboxy terminal coding region of the IL-2$_{ser125}$ gene was purified from an agarose gel. Similarly, pLW32 was digested with XbaI and PstI and the large fragment consisting of the plasmid vector and the ala-IL-2 N-terminal coding sequence was purified. The two purified DNA fragments were pooled and ligated using T$_4$ DNA ligase. The ligated DNA was transformed into competent E. coli K-12 strain MM294. Tetracycline resistant transformants were analyzed by restriction enzyme mapping for the presence of a plasmid containing an ala-IL-2$_{ser125}$ gene, identified as pLW55, which has a new DdeI site not found in pLW32. FIG. 17 is a diagram of pLW55. Cell free extracts of bacterial culture containing pLW55 were found to contain over $10^5$ units of IL-2 activity per ml by the HT-2 cell assay, J. Watson, supra, and S. Gillis, supra. Ala-IL-2$_{ser124}$ protein is identical to the IL-2$_{ser125}$ molecule shown in FIG. 15(b) except that the former includes the initial N-terminal alanine of the native molecule.

A sample of E. coli K-12 strain MM294 transformed with pLW55 was deposited in the American Type Culture Collection on 18 Nov. 1983 and has been assigned ATCC number 39,516.

EXAMPLE 20

Ala-IL-2$_{ser125}$ Production and Purification

E. coli transformed with pLW55 were grown in a fermenter containing the following medium:

| | |
|---|---|
| (NH$_4$) | 150 mM |
| KH$_2$PO$_4$ | 21.6 mM |
| Na$_3$ Citrate | 1.5 mM |
| ZnSO$_4$.7H$_2$O | 30 μM |
| MnSO$_4$.5H$_2$O | 30 μM |
| CuSO$_4$5H$_2$O | 1 μM |
| pH adjusted to 6.50 with 2.5 N NaOH autoclaved | |
| Sterile Additions (post autoclave) | |
| MgSO$_4$.7H2O | 3 mM |
| FeSO$_4$ | 100 μM |
| L-tryptophan | 14 mg/l |
| Thiamine-HCl | 20 mg/l |
| Glucose | 5 g/l |
| Tetracycline | 5 mg/l |
| Ethanol | 2% |
| Casamino acids | 2% |

Dow Corning Antifoam polypropylene glycol, 20% solution, glucose, 50% solution, and KOH, 5N, were added on demand.

The pH of the fermenter was maintained at 6.8 with 5N KOH. Residual glucose was maintained between 5-10 g/l, dissolved oxygen at 40%, and temperature at 37°±1° C. The casamino acids (20% stock solution) to a concentration of 2% were added when the OD$_{680}$ was about 10. Harvest was made three hr after the OD reached about 20.

The harvested material was concentrated and homogenized as in Example 11. Following DTT-heat treatment, the material was centrifuged and the resulting paste was extracted with urea to a final concentration of 4M. The suspension was centrifuged and SDS was added to the solid phase to a concentration of 5%. The solution was applied to a Sephacryl S-200 column and fractions containing IL-2 (by SDS-PAGE) were pooled. The pooled fractions were applied to a Whatman M-40 column packed with 18 micron Vydac C$_4$ 300 Å pore size bonded phase silica gel equilibrated in 0.1% TFA. The IL-2 mutein was eluted with a gradient of 40% to 60% 2-propanol, containing 0.1% TFA, in 160 min. Fractions containing highest IL-2 activities were pooled and found to have specific activities comparable to native IL-2.

Muteins of IL-2 in which the cysteine at position 125 has been replaced with another amino acid, such as the mutein IL-2$_{ser125}$ retain IL-2 activity. They may, therefore, be formulated and used in the same manner as native IL-2. Accordingly, such IL-2 muteins are useful for the diagnosis and treatment (local or systemic) of bacterial, viral, parasitic, protozoan and fungal infections; for augmenting cell-mediated cytotoxicity; for stimulating lymphokine activated killer cell activity; for mediating recovery of immune function of lymphocytes; for augmenting alloantigen responsiveness; for facilitating recovery of immune function in acquired immune deficient states; for reconstitution of normal immunofunction in aged humand and animals; in the development of diagnostic assays such as those employing enzyme amplification, radiolabelling, radioimaging, and other methods known in the art for monitoring IL-2 levels in the diseased state; for the promotion of T cell growth in vitro for therapeutic and diagnostic purposes for blocking receptor sites for lymphokines; and in various other therapeutic, diagnostic and research applications. The various therapeutic and diagnostic applications of human IL-2 have been investigated and reported in S. A. Rosenberg, E. A. Grimm, et al, A. Mazumder, et al, and E. A. Grimm and S. A. Rosenberg. IL-2 muteins may be used by themselves or in combination with other immunologically relevent B or T cells or other therapeutic agents. Examples of relevant cells are B or T cells, natural killer cells, and the like and exemplary therapeutic reagents which may be used in combination with the polypeptides of this invention are the various interferons, especially gamma interferon, B cell growth factor, IL-1 and the like. For therapeutic or diagnostic applications, they may be formulated in nontoxic, nonallergenic, physiologically compatible carrier media such as distilled water, Ringer's solution, Hank's solution, physiological saline and the like. Administrations of the IL-2 muteins to humans or animals may be oral or intraperitoneal or intramuscular or subcutaneous as deemed appropriate by the physician. The amount of IL-2 mutein administered will usually range between about $1 \times 10^4$ and $2 \times 10^8$ units.

Modifications of the above described modes for carrying out the invention that are obvious to those of skill in the fields of genetic engineering, protein chemistry, medicine, and related fields are intended to be within the scope of the following claims.

We claim:

1. A structural gene having a DNA sequence that encodes a synthetic interleukin-2 mutein wherein the cysteine residue at position 125, numbered in accordance with native human interleukin-2, is replaced by a neutral amino acid.

2. The structural gene of claim 1 wherein the neutral amino acid is selected from the group consisting of serine, threonine, glycine, alanine, valine, leucine, isoleucine, histidine, tyrosine, phenylalanine, tryptophan, and methionine.

3. The structural gene of claim 1, wherein the neutral amino acid is serine or threonine.

4. The structural gene of claim 1, wherein the neutral amino acid is serine.

5. The structural gene of claims 1, 2, 3, 4 with or without an initial ATG codon.

6. The structural gene as represented in FIG. 15a, with or without the initial ATG codon.

7. An expression vector that includes the structural gene of claims 1, 2, 3, 4 or 6.

8. The expression vector of claim 7, wherein the vector is pBR322 or pCR1.

9. The plasmid pLW46 having an ATCC accession number 39,452.

10. The plasmid pLW55 having an ATCC accession number 39,516.

11. A host cell transformed with an expression vector that includes a structural gene having a DNA sequence that encodes a synthetic interleukin-2 mutein wherein the cysteine residue at position 125, numbered in accordance with native human interleukin-2, is replaced by a neutral amino acid and said mutein exhibits the biological activity of native human interleukin-2, wherein the host cell is selected from the group consisting of bacteria, yeast, animal, and plant.

12. The host cell of claim 11, wherein the host cell is bacteria.

13. The host cell of claim 12, wherein the bacteria is *E. coli*.

14. The host cell of claims 11, 12 or 13, wherein the neutral amino acid is selected from the group consisting of serine, threonine, glycine, alanine, valine, leucine, isoleucine, histidine, tyrosine, phenylalanine, tryptophan, and methionine.

15. The host cell of claims 11, 12 or 13, wherein the neutral amino acid is serine.

16. *E. coli* transformed by an expression vector which includes the structural gene represented by FIG. 15a, with or without the initial ATG codon.

17. *E. coli* transformed with a plasmid selected from the group consisting of pLW46 and pLW55, and progeny thereof.

* * * * *